United States Patent
deLong et al.

(10) Patent No.: US 6,372,730 B1
(45) Date of Patent: Apr. 16, 2002

(54) 2-DECARBOXY-2-PHOSPHINICO PROSTAGLANDIN F ANALOGS

(75) Inventors: Mitchell Anthony deLong, West Chester; John August Wos, Cincinnati; Biswanath De, Cincinnati; Frank Hallock Ebetino, Cincinnati, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/632,256

(22) Filed: Aug. 3, 2000

Related U.S. Application Data

(60) Provisional application No. 60/147,132, filed on Aug. 4, 1999.

(51) Int. Cl.[7] .............................. A61K 31/66; C07F 9/02
(52) U.S. Cl. ........................................ 514/140; 558/207
(58) Field of Search ........................ 558/207; 514/140

(56) References Cited

U.S. PATENT DOCUMENTS

| | | | | |
|---|---|---|---|---|
| 4,171,331 A | | 10/1979 | Biddlecom et al. .......... | 260/946 |
| 5,312,832 A | | 5/1994 | Chan .......................... | 524/513 |
| 5,409,911 A | * | 4/1995 | Tyler et al. ................... | 514/91 |
| 5,658,897 A | * | 8/1997 | Burk .......................... | 514/118 |
| 6,121,253 A | * | 9/2000 | Han et al. .................... | 514/102 |

FOREIGN PATENT DOCUMENTS

| | | | | |
|---|---|---|---|---|
| WO | WO 99/12895 | 3/1999 | ......... | C07C/405/00 |
| WO | WO 99/12896 | 3/1999 | ......... | C07C/405/00 |
| WO | WO 99/12898 | 3/1999 | ......... | C07C/405/00 |

OTHER PUBLICATIONS

Liljebris et al., "Derivatives of 17–Phenyl–18,19,20–trinor-prostaglandin $F_{2\alpha}$ Isopropyl Ester: Potential Antiglaucoma Agents", *J. Med. Chem.*, vol. 38, pp. 289–304 (1995).

Kluender et al., "The Synthesis of Dimethylphosphonoprostaglandin Analogs", *Prostaglandins and Medicine*, vol. 2, pp. 441–444 (1979).

Kende et al., "Prostaglandin Phosphonic Acids Through Homolytic Halodecarboxylation of Prostaglandins $F_{1\alpha}$ and $F_{2\alpha}$", *Tetrahedron Letters*, vol. 40, pp. 8189–8192 (1999).

* cited by examiner

*Primary Examiner*—Deborah C. Lambkin
(74) *Attorney, Agent, or Firm*—David V. Upite; Carl J. Roof; Mary Pat McMahon

(57) ABSTRACT

The invention provides novel Prostaglandin F analogs. In particular, the present invention is directed to compounds having a structure according to the following formula:

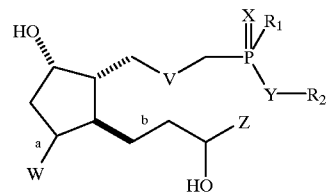

wherein $R_1$, $R_2$, X, Y, V, a, b, W, and Z are defined below.

This invention also includes optical isomers, diastereomers and enantiomers of the formula above, and pharmaceutically—acceptable salts, biohydrolyzable amides, esters, and imides thereof.

The compounds of the present invention are useful for the treatment of a variety of diseases and conditions, such as bone disorders and glaucoma. Accordingly, the invention further provides pharmaceutical compositions comprising these compounds. The invention still further provides methods of treatment for bone disorders and glaucoma using these compounds or the compositions containing them.

14 Claims, No Drawings

2-DECARBOXY-2-PHOSPHINICO PROSTAGLANDIN F ANALOGS

TECHNICAL FIELD

The invention relates to certain novel analogs of naturally occurring Prostaglandin $F_{2\alpha}$. Specifically, the invention relates to novel 2-decarboxy-2-phosphinico Prostaglandin F analogs. The invention further relates to methods of using said novel 2-decarboxy-2-phosphinico Prostaglandin F analogs. Preferred uses include treatment of bone disorders and glaucoma.

CROSS REFERENCE

This application claims priority under Title 35, United States Code 119(e) from Provisional Application Ser. No. 60/147,132, filed Aug. 4, 1999.

BACKGROUND OF THE INVENTION

The naturally occurring prostaglandin, $PGF_{2\alpha}$, is a twenty-carbon (C-20) unsaturated fatty acid derived from arachidonic acid. Using standard prostaglandin nomenclature, $PGF_{2\alpha}$ possesses alpha-hydroxyl groups at both $C_9$ and at $C_{11}$ on the cyclopentane ring, a cis double bond between $C_5$ and $C_6$, and a trans double bond between $C_{13}$ and $C_{14}$. Thus $PGF_{2\alpha}$ has the following structure:

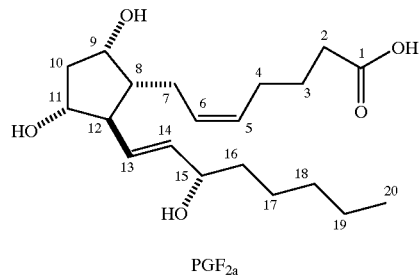

$PGF_{2a}$

Analogs of $PGF_{2\alpha}$ are useful for the treatment of several medical conditions including, for example: ocular disorders, such as glaucoma; circulatory disorders, gastrointestinal disorders; fertility control; and bone disorders, such as osteoporosis. Information regarding the biological effects of Prostaglandin F analogs is disclosed in the following references: PCT Publication No. WO 99/12895, 1999; PCT Publication No. WO 99/12896, 1999; PCT Publication No. WO 99/12898; Chem. Abstr. 1999, 194116 "Molecular mechanisms of diverse actions of prostanoid receptors", Biochimica et Biophysica Acta, 1259 (1995) 109–120; U.S. Pat. No. 3,776,938 issued to Bergstrom, S., and Sjovall, J., Dec. 4, 1973; U.S. Pat. No. 3,882,241 issued to Pharriss, G., May 6, 1975; G.B. Patent No. 1,456,512 (1976) issued to Pfizer Inc., Bundy, G. L.; Lincoln, F. H., "Synthesis of 17-Phenyl-18,19,20-trinor prostaglandins I. The PGI Series", Prostaglandins Vol. 9 (1975) pp. 1–4.; CRC Handbook of Eicosanoids: Prostaglandins and Related Lipids Vol. 1, Chemical and Biochemical Aspects, Parts A & B, A. L. Willis, eds., CRC Press (1987); Liljebris, C.; et. al. "Derivatives of 17-Phenyl-18,19,20-trinorprostaglandin F2a Isopropyl Ester: Potential Antiglaucoma Agents", Journal of Medicinal Chemistry Vol. 38, (1995), pp. 289–304; Collins, P. W.; Djuric, S. W. "Synthesis of Therapeutically Useful Prostaglandin and Prostacyclin Analogs", Chemical Reviews 93 (1993), pp. 1533–1564.

All naturally occurring prostaglandins, including $PGF_{2\alpha}$, possess a carboxylic acid moiety at the $C_1$ position. The carboxylic acid moiety is a site for metabolic degradation by beta oxidation, which contributes to the rapid metabolism of the naturally occurring prostaglandins. Attempts to prevent beta oxidation by modifying the carboxylic acid moiety at the 1 position as an ester moiety, an amide moiety, a sulfonamide moiety, and as a tetrazole moiety are known in the art (See e.g. PCT Publication No. WO 99/12895, 1999; PCT Publication No. WO 99/12896, 1999; PCT Publication No. WO 99/12898).

However, such modifications have either resulted in only modest increases in half-life (such as the esters) or resulted in compounds with diminished potency.

Prostaglandin F analogs wherein $C_1$, itself is replaced with a heteroatom have also been described in the art. For example, PGF analogs containing a sulfonic acid moiety at $C_1$, (The chemistry of prostaglandins containing the sulfo group. Iguchi, Y.; Kori, S.;

Hayashi, M. J Org. Chem., 40, pp. 521–523 1975) and PGF analogs containing a phosphonic acid moiety at C, (The Synthesis of dimethylphosphonoprostaglandin analogs, Kluender, H. C. & Woessner, W. Prostaglandins and Medicine, 2: pp.441–444, 1979) have been disclosed. However, such compounds suffer from significantly diminished potency.

Further research in the area of heteroatom—containing $C_1$, replacements has been hampered by the lack of a general synthetic route to advanced or key intermediates that would allow for the rapid preparation of a multitude of variants to replace $C_1$. The Corey route to prostaglandins was specifically designed for a carboxcyclic acid moiety, and modifications which create reagents with relatively acidic protons are either incompatible with this route or cause significant optimization of this difficult step for each new $C_1$ replacement. Syntheses of Prostaglandin F analogs via the Corey route are described in the following references: Corey, E. J.; Weinshenker, N. M.; Schaaf, T. K.; Huber, W J Am. Chem. Soc., 1969, 91, 5675 and Corey, E. J.; Schaaf, T. K.; Huber, W; Koelliker, U.; Weinshenker, N. M.; J. Am. Chem. Soc., 1970, 92, 397.

Thus, while a few Prostaglandin F analogs wherein $C_1$ has been replaced with a heteroatom—containing moiety have been disclosed, there is a continuing need for suitable $C_1$ replacements that result in potent, selective Prostaglandin F analogs for the treatment of a variety diseases and conditions.

SUMMARY OF THE INVENTION

The invention provides novel Prostaglandin F analogs. In particular, the present invention is directed to compounds having a structure according to the following formula:

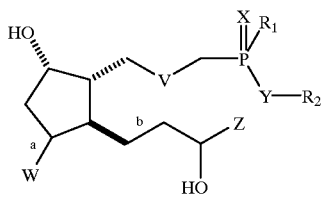

wherein $R_1$, $R_2$, X, Y, V, a, b, W, and Z are defined below.

This invention also includes optical isomers, diastereomers and enantiomers of the formula above, and pharmaceutically—acceptable salts, biohydrolyzable amides, esters, and imides thereof.

The compounds of the present invention are useful for the treatment of a variety of diseases and conditions, such as bone disorders and glaucoma. Accordingly, the invention further provides pharmaceutical compositions comprising these compounds. The invention still further provides methods of treatment for bone disorders and glaucoma using these compounds or compositions containing them.

DETAILED DESCRIPTION OF THE INVENTION

The invention is directed to novel 2-decarboxy-2-phosphinico Prostaglandin F analogs, pharmaceutical compositions comprising these compounds, and methods of treating a variety of disorders by administering these compounds.

Definitions and Usage of Terms

"Alkyl" is a saturated or unsaturated hydrocarbon chain. Unless otherwise specified (e.g. see "$C_4$ alkyl", "$C_1$ alkyl", "$C_m$ alkyl" and "$C_p$ alkyl" below), alkyl chains have 1 to 18 carbon atoms, preferably 1 to 12, more preferably 1 to 6, more preferably still 1 to 4 carbon atoms. Alkyl chains may be straight or branched. Preferred branched alkyl have one or two branches, preferably one branch. Unsaturated alkyl have one or more double bonds and/or one or more triple bonds. Preferred unsaturated alkyl have one or two double bonds or one triple bond, more preferably one double bond. Alkyl chains may be unsubstituted or substituted with from 1 to about 4 substituents unless otherwise specified. Preferred substituted alkyl are mono-, di-, or trisubstituted. Preferred alkyl substituents include cyano, halo, hydroxy, aryl (e.g., phenyl, tolyl, alkyloxphenyl, alkyloxycarbonylphenyl, halophenyl), heterocyclyl, and heteroaryl.

"Aromatic ring" is an aromatic hydrocarbon ring system. Aromatic rings are monocyclic or fused bicyclic ring systems. Monocyclic aromatic rings contain from about 5 to about 10 carbon atoms, preferably from 5 to 7 carbon atoms, and most preferably from 5 to 6 carbon atoms in the ring. Bicyclic aromatic rings contain from 8 to 12 carbon atoms, preferably 9 or 10 carbon atoms in the ring. Aromatic rings may be unsubstituted or substituted with from 1 to about 4 substituents on the ring. Preferred aromatic ring substituents include: halo, cyano, lower alkyl, heteroalkyl, haloalkyl, phenyl, phenoxy or any combination thereof. More preferred substituents include lower alkyl, cyano, halo and haloalkyl.

"Biohydrolyzable amide" is an amide moiety that does not interfere with the therapeutic activity of the compound, or that is readily metabolized by a human or other mammal.

"Biohydrolyzable ester" is an ester moiety that does not interfere with the therapeutic activity of the compound, or that is readily metabolized by a human or other mammal.

"Biohydrolyzable imide" is an imide moiety that does not interfere with the therapeutic activity of the compound, or that is readily metabolized by a human or other mammal.

"$C_4$ alkyl" is an alkyl chain having 4 carbon member atoms. $C_4$ alkyl may be staurated or unsaturated with one or two double bonds (cis or trans), one triple bond, or one double bond (cis or trans) and one triple bond. Preferred unsaturated $C_4$ alkyl have one double bond. $C_4$ alkyl may be unsubstituted or substituted with one or two substituents. Preferred substituents include lower alkyl, lower heteroalkyl, cyano, halo, and haloalkyl. More preferred substituents are cyano and halo.

"$C_1$ alkyl" is an alkyl chain having "1" carbon member atoms. $C_1$ alkyl may be staurated or unsaturated with one trans double bond or one triple bond. Preferred $C_1$ alkyl are saturated. Preferred unsaturated $C_1$ alkyl have one trans double bond. $C_1$ alkyl may be unsubstituted or substituted with from 1 to about 3 substituents. Preferred substituents include lower alkyl, lower heteroalkyl, cyano, halo, and haloalkyl.

"$C_m$ alkyl" is an alkyl chain having "m" carbon member atoms. $C_m$ alkyl may be staurated or unsaturated with one trans double bond or one triple bond. Preferred unsaturated $C_m$ alkyl have one triple bond. $C_m$ alkyl may be unsubstituted or substituted with one or two substituents. Preferred $C_m$ alkyl are unsubstituted. Preferred substituents include lower alkyl, lower heteroalkyl, cyano, halo, and haloalkyl.

"$C_p$ alkyl" is an alkyl chain having "p" carbon member atoms. $C_p$ alkyl may be staurated or unsaturated with one trans double bond or one triple bond. Preferred unsaturated $C_m$ alkyl have one triple bond. Unsaturated $C_p$ alkyl are unsubstituted. Saturated $C_p$ alkyl may be unsubstituted or substituted with one or two substituents. Preferred $C_p$ alkyl are unsubstituted. Preferred substituents include lower alkyl, lower heteroalkyl, cyano, halo, and haloalkyl.

"Carbocyclic aliphatic ring" is a saturated or unsaturated hydrocarbon ring. Carbocyclic aliphatic rings are not aromatic. Carbocyclic aliphatic rings are monocyclic, or are fused, spiro, or bridged bicyclic ring systems. Monocyclic carbocyclic aliphatic rings contain from about 4 to about 10 carbon atoms, preferably from 4 to 7 carbon atoms, and most preferably from 5 to 6 carbon atoms in the ring. Bicyclic carbocyclic aliphatic rings contain from 8 to 12 carbon atoms, preferably from 9 to 10 carbon atoms in the ring. Carbocyclic aliphatic rings may be unsubstituted or substituted with from 1 to about 4 substituents on the ring. Preferred carbocyclic aliphatic ring substituents include: halo, cyano, lower alkyl, heteroalkyl, haloalkyl, phenyl, phenoxy or any combination thereof More preferred substituents include halo and haloalkyl. Preferred carbocyclic aliphatic rings include cyclopentyl, cyclohexyl, cyclohexenyl, cycloheptyl, and cyclooctyl.

"Halo" is fluoro, chloro, bromo or iodo. Preferred halo are fluoro, chloro and bromo; more preferred are chloro and fluoro.

"Haloalkyl" is a straight, branched, or cyclic hydrocarbon substituted with one or more halo substituents. Preferred haloalkyl are $C_1$—$C_{12}$; more preferred are $C_1$—$C_6$; more preferred still are $C_1$—$C_3$. Preferred halo substituents are fluoro and chloro. The most preferred haloalkyl is trifluoromethyl.

"Heteroalkyl" is a saturated or unsaturated chain containing carbon and at least one heteroatom, wherein no two heteroatoms are adjacent. Heteroalkyl chains contain from 1 to 18 member atoms (carbon and heteroatoms) in the chain, preferably 1 to 12, more preferably 1 to 6, more preferably still 1 to 4. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Preferred unsaturated heteroalkyl have one or two double bonds or one triple bond, more preferably one double bond. Heteroalkyl chains may be unsubstituted or substituted with from 1 to about 4 substituents unless otherwise specified. Preferred heteroalkyl are unsubstituted. Preferred heteroalkyl substituents include halo, aryl (e.g., phenyl, tolyl, alkyloxyphenyl, alkyloxycarbonylphenyl, halophenyl), heterocyclyl, heteroaryl. For example, alkyl chains substituted with the following substituents are heteroalkyl: alkoxy (e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonylphenylthio), amino (e.g., amino, mono- and di- $C_1$—$C_3$ alkanylamino, methylphenylamino, methylbenzylamino, $C_1$—$C_3$ alkanylamido, carbamamido, ureido, guanidino).

"Heteroatom" is a nitrogen, sulfur, or oxygen atom. Groups containing more than one heteroatom may contain different heteroatoms. As used herein, halogens are not heteroatoms.

"Heterocyclic aliphatic ring" is a saturated or unsaturated ring containing carbon and from 1 to about 4 heteroatoms in the ring, wherein no two heteroatoms are adjacent in the ring and no carbon in the ring that has a heteroatom attached to it also has a hydroxyl, amino, or thiol group attached to it. Heterocyclic aliphatic rings are not aromatic. Heterocyclic aliphatic rings are monocyclic, or are fused or bridged bicyclic ring systems. Monocyclic heterocyclic aliphatic rings contain from about 4 to about 10 member atoms (carbon and heteroatoms), preferably from 4 to 7, and most preferably from 5 to 6 member atoms in the ring. Bicyclic heterocyclic aliphatic rings contain from 8 to 12 member atoms, preferably 9 or 10 member atoms in the ring. Heterocyclic aliphatic rings may be unsubstituted or substituted with from 1 to about 4 substituents on the ring. Preferred heterocyclic aliphatic ring substituents include: halo, cyano, lower alkyl, heteroalkyl, haloalkyl, phenyl, phenoxy or any combination thereof. More preferred substituents include halo and haloalkyl. Preferred heterocyclic aliphatic rings include piperzyl, morpholinyl, tetrahydrofuranyl, tetrahydropyranyl and piperdyl.

"Heteroaromatic ring" is an aromatic ring system containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 in the ring. Bicyclic heteroaromatic rings contain from 8 to 12 member atoms, preferably 9 or 10 member atoms in the ring. Heteroaromatic rings may be unsubstituted or substituted with from 1 to about 4 substituents on the ring. Preferred heteroaromatic ring substituents include: halo, cyano, lower alkyl, heteroalkyl, haloalkyl, phenyl, phenoxy or any combination thereof. More preferred substituents include halo, haloalkyl, and phenyl. Preferred heteroaromatic rings include thienyl, thiazolo, purinyl, pyrimidyl, pyridyl, and furanyl. More preferred heteroaromatic rings include thienyl, furanyl, and pyridyl. The most preferred heteroaromatic ring is thienyl.

"Lower alkyl" is an alkyl chain comprised of 1 to 4, preferably 1 to 3 carbon member atoms, more preferably 1 or 2 carbon member atoms. Lower alkyl may be saturated or unsaturated. Preferred lower alkyl are saturated. Lower alkyl may be unsubstituted or substituted with one or about two substituents. Preferred substituents on lower alkyl include cyano, halo, triflouromethyl, and hydroxy.

"Lower heteroalkyl" is a heteroalkyl chain comprised of 1 to 4, preferably 1 to 3 member atoms, more preferably 1 to 2 member atoms. Lower heteroalkyl contain one or two heteroatom member atoms. Preferred lower heteroalkyl contain one heteroatom member atom. Lower heteroalkyl may be saturated or unsaturated. Preferred lower heteroalkyl are saturated. Lower heteroalkyl may be unsubstituted or substituted with one or about two substituents. Preferred substituents on lower heteroalkyl include cyano, halo, triflouromethyl, and hydroxy.

"$M_4$ heteroalkyl" is a heteroalkyl chain having 4 member atoms. $M_4$ heteroalkyl contain one or two heteroatom member atoms. $M_4$ heteroalkyl containing 1 heteroatom member atom may be saturated or unsaturated with one double bond (cis or trans) or one triple bond. Preferred $M_4$ heteroalkyl containing 2 heteroatom member atoms are saturated. Preferred unsaturated $M_4$ heteroalkyl have one double bond. $M_4$ heteroalkyl may be unsubstituted or substituted with one or two substituents. Preferred substituents include lower alkyl, lower heteroalkyl, cyano, halo, and haloalkyl.

"$M_1$ heteroalkyl" is a heteroalkyl chain having "1" member atoms. $M_1$ heteroalkyl contain one or two heteroatom member atoms. Preferred $M_1$ heteroalkyl have one heteroatom member atom. $M_1$ heteroalkyl may be saturated or unsaturated with one trans double bond or one triple bond. Preferred $M_1$ heteroalkyl are saturated. $M_1$ heteroalkyl may be unsubstituted or substituted with from 1 to about 3 substituents. Preferred substituents include lower alkyl, lower heteroalkyl, and haloalkyl.

"$M_n$ heteroalkyl" is a heteroalkyl chain having "n" member atoms. $M_n$ heteroalkyl contain one heteroatom member atom. $M_n$ heteroalkyl may be staurated or unsaturated with one triple bond. Preferred $M_n$ heteroalkyl are saturated. $M_n$ heteroalkyl may be unsubstituted or substituted with one or two substituents. Preferred substituents include lower alkyl, lower heteroalkyl, and haloalkyl.

"$M_q$ heteroalkyl" is a heteroalkyl chain having "q" member atoms. $M_q$ heteroalkyl contain one heteroatom member atom. $M_q$ heteroalkyl are staurated. $M_q$ heteroalkyl may be unsubstituted or substituted with one or two substituents. Preferred substituents include lower alkyl, lower heteroalkyl, cyano, halo, and haloalkyl.

"Member atom" refers to a polyvalent atom (C, O, N, or S atom) in a chain or ring system that continues the chain or ring system. For example, in benzene the six carbon atoms are member atoms and the six hydrogen atoms are not member atoms.

"Pharmaceutically—acceptable salt" refers to a cationic salt formed at any acidic (e.g., hydroxamic acid) group, or an anionic salt formed at any basic (e.g., amino) group. Such salts are well known in the art. See e.g: World Patent Publication 87/05297, Johnston et al., published Sep. 11, 1987, incorporated herein by reference. Such salts are made by methods known to one of ordinary skill in the art. It is recognized that the skilled artisan may prefer one salt over another for improved solubility, stability, formulation ease, price and the like. Determination and optimization of such salts is within the purview of the skilled artisan's practice. Preferred cationic salts include the alkali metal salts (such as sodium and potassium), and alkaline earth metal salts (such as magnesium and calcium) and organic salts. Preferred anionic salts include the halides (such as chloride salts), sulfonates, carboxylates, phosphates, and the like. Clearly contemplated in such salts are addition salts that may provide an optical center where once there was none. For example, a chiral tartrate salt may be prepared from the compounds of the invention. This definition includes such chiral salts.

"Phenyl" is a six-membered monocyclic aromatic ring which may or may not be substituted with from about 1 to about 4 substituents. The substituents may be substituted at the ortho, meta or para position on the phenyl ring, or any combination thereof. Preferred phenyl substituents include: halo, cyano, lower alkyl, heteroalkyl, haloalkyl, phenyl, phenoxy or any combination thereof. More preferred substituents on the phenyl ring include halo and haloalkyl. The most preferred substituent is halo.

Compounds

The invention involves compounds having the following structure:

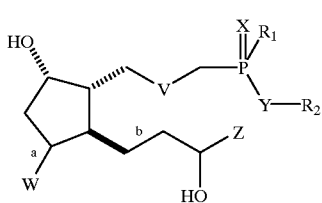

Formula I

In Formula I above, $R_1$ is H or lower alkyl. Preferred $R_1$ is lower alkyl. More preferred $R_1$ is methyl and ethyl. The most preferred $R_1$ is methyl.

In Formula I above, $R_2$ is H, alkyl, heteroalkyl, carbocyclic aliphatic ring, heterocyclic aliphatic ring, aromatic ring, or heteroaromatic ring. Preferred $R_2$ is H and alkyl. More preferred $R_2$ is H and lower alkyl.

In Formula I above, X is O or S. Preferred X is O.

In Formula I above, Y is O, S or NH. Preferred Y is O and NH. The most preferred Y is O.

In Formula I above, V is $C_4$ alkyl or $M_4$ heteroalkyl. Preferred V is $C_4$ alkyl. More preferred V is unsubstituted $C_4$ alkyl.

In Formula I above, a is single bond, cis double bond, or trans double bond.

In Formula I above, b is single bond, trans double bond, or triple bond.

In Formula I above, when a is single bond, W is OH or $N(R_3)(OR_4)$; wherein $R_3$ is H, lower alkyl, or lower heteroalkyl and $R_4$ is H, lower alkyl, or lower heteroalkyl. Preferred $R_3$ is H and lower alkyl. More preferred $R_3$ is H and methyl. Preferred $R_4$ is H and lower alkyl. More preferred $R_4$ is H and methyl. The most p referred $R_4$ is H.

In Formula I above, when a is cis double bond or trans double bond, W is $N(OR_4)$; wherein $R_4$, is as defined above.

In Formula I above, Z is $C_1$ alkyl, $M_1$ heteroalkyl, $C_m$ alkyl-G', $M_n$ heteroalkyl-G', $C_p$ alkyl-G", or $M_q$ heteroalkyl-G"; wherein l is an integer from about 3 to about 7, preferably from about 4 to about 7; m is an integer from 0 to about 5, preferably from about 1 to about 4, more preferably still about 2 or 3, most preferably 2; n is an integer from about 2 to about 5, preferably about 2 or 3; p is an integer from 0 to about 3, preferably 0 to about 2, more preferably 0 or about 1; q is 2 or 3, preferably 2; G' is monocyclic carbocyclic aliphatic ring, monocyclic heterocyclic aliphatic ring, monocyclic aromatic ring, or monocyclic heteroaromatic ring; G" is bicyclic carbocyclic aliphatic ring, bicyclic heterocyclic aliphatic ring, bicyclic aromatic ring, or bicyclic heteroaromatic ring. Preferred G' is monocyclic aromatic ring or monocyclic heteroaromatic ring. Preferred G" is bicyclic aromatic ring or bicyclic heteroaromatic ring.

The invention includes pharmaceutically—acceptable salts, or biohydrolyzable amides, esters, or imides of the above structure. The invention also includes optical isomers, diastereomers and enantiomers of the above structure. Thus, at all stereocenters where stereochemistry is not defined (e.g. $C_{11}$ and $C_{15}$), both epimers are envisioned. Preferred stereochemistry at $C_{11}$ and $C_{15}$ mimics that of naturally occurring $PGF_{2\alpha}$.

It has been discovered that the novel PGF analogs of the subject invention are useful for treating bone disorders, especially those that require a significant increase in bone mass, bone volume, or bone strength. Surprisingly, the compounds of the subject invention have been found to provide the following advantages over known bone disorder therapies: (1) An increase trabecular number through formation of new trabeculae; (2) An increase in bone mass and bone volume while maintaining a more normal bone turnover rate; and/or (3) An increase in bone formation at the endosteal surface without increasing cortical porosity.

In order to determine and assess pharmacological activity, testing of the subject compounds in animals is carried out using various assays known to those skilled in the art. For example, the bone activity of the subject compounds can be conveniently demonstrated using an assay designed to test the ability of the subject compounds to increase bone volume, mass, or density. An example of such assays is the ovariectomized rat assay.

In the ovariectomized rat assay, six-month old rats are ovariectomized, aged 2 months, and then dosed once a day subcutaneously with a test compound. Upon completion of the study, bone mass and/or density can be measured by dual energy x-ray absorptometry (DXA) or peripheral quantitative computed tomography (pQCT), or micro computed tomography (mCT). Alternatively, static and dynamic histomorphometry can be used to measure the increase in bone volume or formation.

Pharmacological activity for glaucoma can be demonstrated using assays designed to test the ability of the subject compounds to decrease intraocular pressure. Examples of such assays are described in the following reference, incorporated herein: C. liljebris, G. Selen, B. Resul, J. Sternschantz, and U. Hacksell, "Derivatives of 17- Phenyl-18,19,20-trinorprostaglandin $F_{2\alpha}$Isopropyl Ester: Potential Antiglaucoma Agents", *Journal of Medicinal Chemistry*, Vol. 38 No. 2 (1995), pp. 289–304.

The following non-limiting examples illustrate the compounds of the present invention:

EXAMPLE 1

Preparation of 5-(3-hydroxy-5-(2-fluorophenyl)pent-1-enyl)-4-(6-(methyl(hydroxyphosphoryl))-hex-2-enyl) cyclopentane-1,3-diol, sodium salt (Elf):

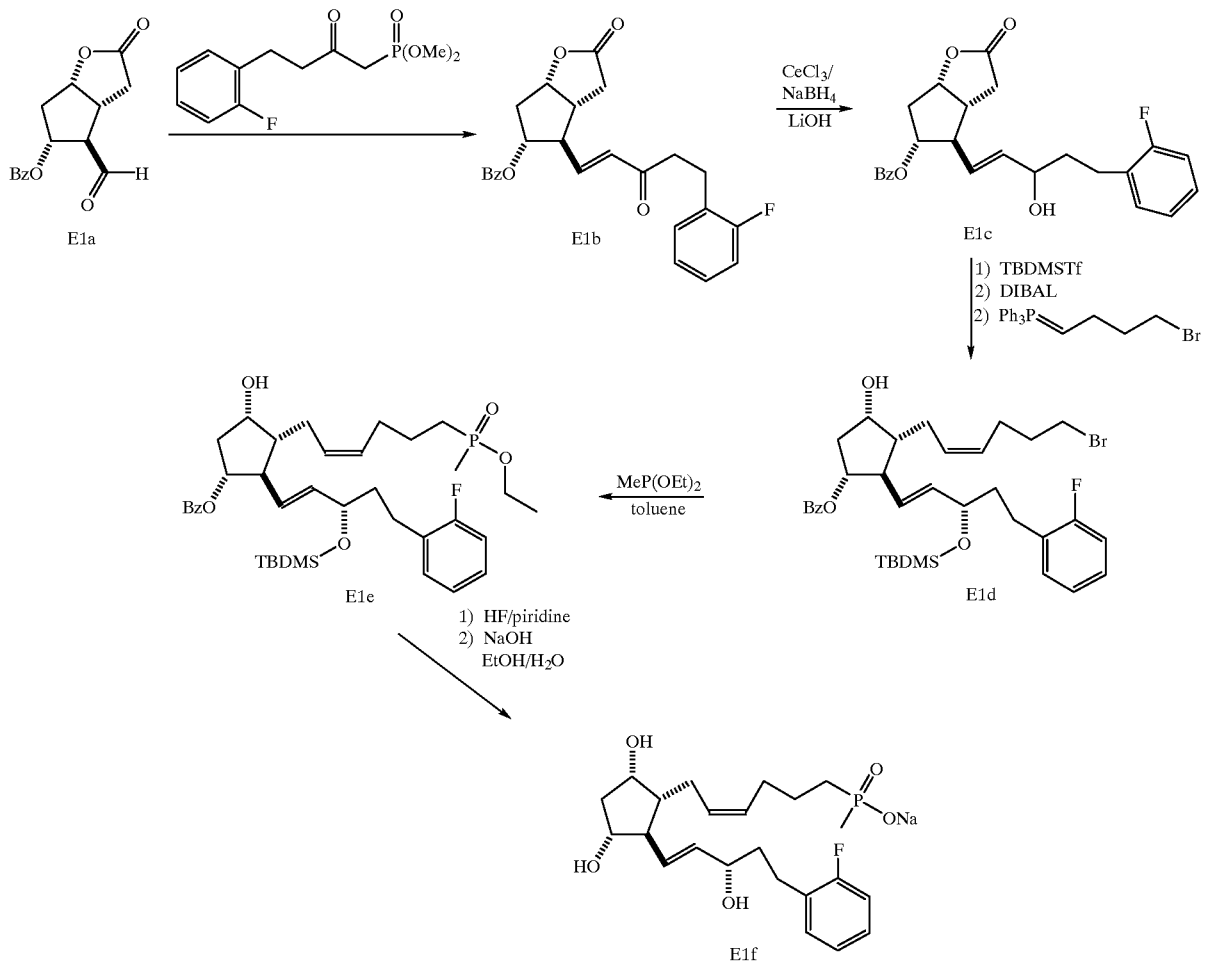

a. 6-(5-(2-fluorophenyl)-3-oxopent-1-enyl)-7-benzyloxy-2-oxabicyclo [3.3.0] octan-3-one (E1b): In a flame-dried, round-bottomed flask equipped with a magnetic stirbar, dimethyl-4-(2-fluorophenyl)-2-oxo-butylphosphonate (1.43 equiv.) is placed in dimethoxyethane (DME) and water. To this solution is added lithium bromide (1.65 equiv.), triethylamine (1.65 equiv), and commercially—available Corey Aldehyde (E1a) (1.0 equiv.). The solution is stirred at room temperature for 48 hours. At this point, additional triethylamine and water is added and the solution is stirred for an additional hour. The solution is poured into brine and extracted with 3 portions of ethyl acetate. The organic layers are combined, dried over anhydrous $M_gSO_4$, filtered, and concentrated under reduced pressure. Purification is effected by silica gel column chromatography (dichloromethane/methanol 19/1) to give 6-(5-(2-fluorophenyl)-3-oxopent-1-enyl)-7-benzyloxy-2-oxabicyclo [3.3.0] octan-3-one (E1b).

b. 6-(5-(2-fluoropbenyl)-3-hydroxypent-1-enyl)-7-benzyloxy-2-oxabicyclo [3.3.0] octan-3-one (E1c): In a flame-dried round-bottomed flask equipped with a stirbar, E1b (1.0 equiv.) and cerium trichloride (1.05 equiv.) are placed in methanol. The solution is stirred at room temperature for 5 minutes. The solution is then cooled to −10° C. and sodium borohydride (1.02 equiv.) in methanol is added slowly. The solution is stirred at −10° C. for 3 hours. The mixture is treated with water and the pH brought between 6 and 7 with 1N hydrochloric acid. The mixture is extracted twice with ethyl acetate, and the organic layers are combined, dried over anhydrous $M_gSO_4$, filtered, and concentrated under reduced pressure. Purification is effected by silica gel column chromatography (3–5 % methanol in dichloromethane) to give the 15 (R) epimer and the 15 (S) epimer of 6-(5-(2-fluorophenyl)-3-hydroxypent- 1 -enyl)-7-benzyloxy-2-oxabicyclo [3.3.0] octan-3-one (E1c).

c. 2-decarboxy-2-bromo 11-benzoyl, -15-tert-butyl dimethylsilyl 17-trinor-17-(2-fluorophenyl) $PGF_{2a}$(E1d): In a round-bottomed flask with a magnetic stir bar, a solution of E1c (1 equiv.) is stirred in $CH_2Cl_2$. To this solution, 2,6-lutidine (1.9 equiv.) is added dropwise at −78° C. followed by tertbutyldimethylsilylltriflate (TBDMSOTf) (1.8 equiv.). The reaction is stirred for 30 minutes at −78° C. and then warmed to 25° C. overnight. The reaction is then quenched with water. The organic layer is washed with water, dried over $M_gSO_4$, and concentrated in vacuo to give a product which is subjected to flash chromatography on silica gel eluting with hexanes then 1% MeOH in $CH_2Cl_2$. The product is then washed with 0.1N HCl, water, and brine and then thoroughly dried. Separately, to a suspension of (4-bromobutyl) triphenylphosphonium bromide (2.2 equiv) in THF at 0° C. under $N_2$, a solution of KHMDS (4.4 equiv.) is added dropwise. The resulting reaction mixture is stirred for 1 hour at 25° C. To the reaction mixture above at −78°

C. is added a solution of the dried silyl-protected product (1 equiv.) in THF. The reaction mixture is allowed to warm to 25° C. overnight. The reaction is quenched with water at 0° C. and the pH is adjusted to 3.5–4.0 with 1N HCl. The water phase is extracted with EtOAc and the combined organic phase is dried over $M_gSO_4$ and concentrated in vacuo to give the crude alkene, which is purified via flash chromatography on silica gel eluting with 30% EtOAc in hexanes yielding 2-decarboxy-2-bromo 11-benzoyl,-15-tert-butyldimethylsilyl-17-trinor-17-(2-fluorophenyl)$PGF_{2a}$ (E1d).

d. 5-(3-silyloxy-5-(2-fluorophenyl)pent-1-enyl)-4-(6 (methyl (ethoxyphosphoryl))hex-2-enyl)-1-benzoyloxy-3-hydroxy-cyclopentane (E1e): A mixture of E1d, diethyl methylphosphonite, and toluene is stirred at 100° C. for 6 hours. The solvents are evaporated and the residue is purified by dry-flash column chromatography ($SiO_2$, 5–25% 2-propanol in 20% dichloromethane-hexane). Appropriate fractions are concentrated, diluted with water, and extracted with ether three times. The combined extracts are washed with water, dried (brine, then filtered over $Na_2SO_4$), and evaporated to give 5-(3-silyloxy-5-(2-fluorophenyl)pent-1-enyl)-4-(6-(methyl(ethoxyphosphoryl))hex-2-enyl)-1-benzoyloxy- 3-hydroxy-cyclopentane (E1e).

e. 5-(3-hydroxy-5-(2-fluorophenyl)pent-1-enyl)-4-(6-(methyl(hydroxyphosphoryl))hex-2-enyl)cyclopentane-1,3-diol, sodium salt (E1f):

Without further purification to the crude reaction mixture of the 2-decarboxy-2-(O-ethyl-P-methylphosphinico) prostaglandin derivative E1e, 3 mL of acetonitrile and 1.1 equivalents of HF/Pyridine are added while the flask is kept at 0° C. After 3 hours at 0° C., the reaction is quenched with saturated aqueous NaCl. The aqueous layer is extracted three times with $CH_2Cl_2$. The organic layers are combined and washed three times with 1N HCl, brine, and dried over sodium sulfate. After column chromatography, (7:3, Hexane: ethyl acetate) the silyl-free product is obtained. To this is added 95% ethanol and 2.5 M aqueous sodium hydroxide and is stirred at reflux for 3 hours. The ethanol is evaporated and the residue is diluted with water and is washed with ethyl acetate two times. The combined washes are extracted with water, the combined aqueous phases are then acidified with 2.5M aqueous hydrochloric acid and extracted with ethyl acetate five times. The combined extracts are dried (brine, $Na_2SO_4$) and evaporated to give 5-(3-hydroxy-5-(2-fluorophenyl)pent-1-enyl)-4-(6-(methyl (hydroxyphosphoryl))hex-2-enyl)cyclopentane-1,3-diol, sodium salt (E1f).

EXAMPLES 2–9

Examples 2–9 are prepared using substantially the same procedure as that described in Example 1, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

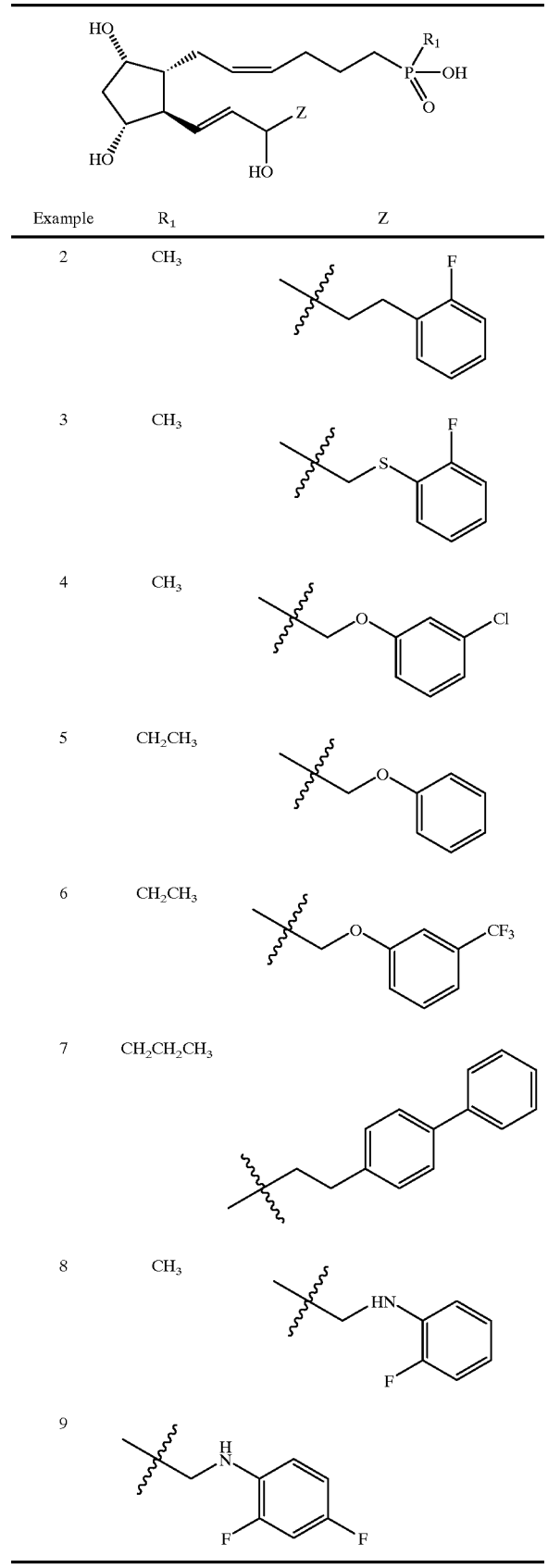

EXAMPLE 10

Preparation of 5-(3-hydroxy-4-phenoxybut-1-enyl)-4-(6-(methyl(hydroxyphosphoryl))hex-2-enyl)cyclopentane-1,3-diol, sodium salt (E10e):

b. 2-decarboxy-2-iodo-16-phenoxy-16-tetranor-$PGF_{2\alpha}$triacetate (E10c): Oxalyl chloride is added to a solution of 16-phenoxy-16-tetranor-$PGF_{2\alpha}$triacetate (E10b) and dimethylformamide in dichloromethane. The mixture is allowed to stand at room temperature for 30 minutes and is

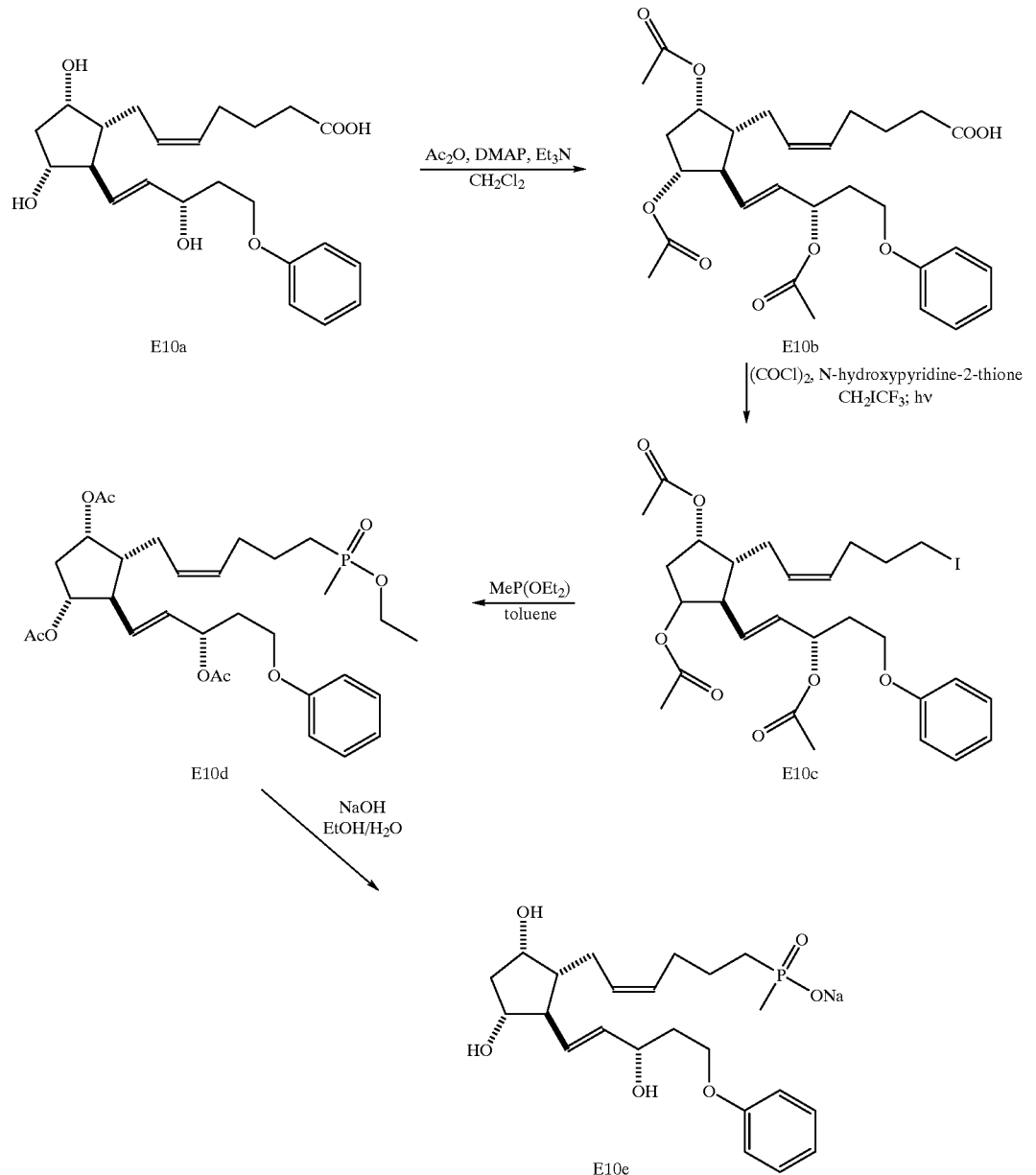

a. 16-phenoxy-16-tetranor-$PGF_{2\alpha}$triacetate (E10b): A mixture of 16-phenoxy-16-tetranor-$PGF_{2\alpha}$(E2a) (commercially—available from Cayman Chemical Company), DMAP, dichloromethane, triethylamine, and acetic anhydride (0.70 mL, 7.3 mmol) is stirred at room temperature for 10 hours and is then stored in a freezer overnight. The mixture is concentrated and the residue is diluted with saturated aqueous sodium carbonate and is stirred at room temperature for 3 hours. The mixture is acidified with 1 M aqueous hydrochloric acid and is then extracted with ethyl acetate five times. The combined extracts are dried (brine, $Na_2SO_4$) and evaporated to give 16-phenoxy-16-tetranor-$PGF_{2\alpha}$triacetate (E10b).

then concentrated. The residue is taken up in dichloromethane. Separately, a mixture of the sodium salt of N-hydroxypyridine-2-thione, DMAP, and dichloromethane under argon is brought to reflux by irradiation with a 250 Watt General Electric floodlamp. To this mixture is added 1,1,1-trifluoro-2-iodoethane, followed by the solution of acid chloride which is added over 15 minutes. Irradiation is continued for 45 minutes and then the mixture is concentrated and purified by dry-flash column chromatography ($SiO_2$, 5–45% ethyl acetate-hexane) to give 2-decarboxy-2-iodo-16-phenoxy-16-tetranor-$PG_{2\alpha}$triacetate (E10c).

c. 2-decarboxy-2-(O-ethyl-P-methylphosphinico)-16-phenoxy-16-tetranor-$PGF_{2\alpha}$(E10d): A mixture of E10c, diethyl methylphosphonite, and toluene is stirred at 100° C. for 7 hours. The solvents are evaporated and the residue is purified by SiO$_2$ column chromatography (5–25% 2-propanol in 20% dichloromethane-hexane). Appropriate fractions are concentrated, diluted with water and extracted with ethyl acetate three times. The combined extracts are washed with water, dried (brine, Na$_2$SO$_4$), and evaporated to give 2-decarboxy-2-(O-ethyl-P-methylphosphinico)-16-phenoxy-16-tetranor-PGF$_{2\alpha}$, triacetate (E10d).

d. 5-(3-hydroxy4-phenoxybut-1-enyl)-4-(6-(methyl(hydroxyphosphoryl))hex-2-enyl)cyclopentane-1,3-diol, sodium salt (E10e): A mixture of E10d, 95% ethanol, and 2.5M aqueous sodium hydroxide is stirred at reflux for 3 hours. The mixture is diluted with water and is washed with ethyl acetate two times. The combined washes are extracted with water. The combined aqueous phases are acidified with 1 M aqueous hydrochloric acid and extracted with ethyl acetate four times. The combined extracts are dried (brine, Na$_2$SO$_4$) and are evaporated. The residue is taken up in methanol and stirred with Amberlite CG-50 (Na form) for 15 minutes. The resin is removed by filtration and the filtrate is concentrated to give 5-(3-hydroxy-4-phenoxybut-1-enyl)-4-(6-(methyl(hydroxyphosphoryl))hex-2-enyl)cyclopentane-1,3-diol, sodium salt (E10e).

EXAMPLES 11–20

Examples 11–20 are prepared using substantially the same procedure as that described in Example 10, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

For some structures, it is advantageous to construct a complete prostaglandin using known means and then transform the completed prostaglandin into the phosphinic acid using substantially the same means as described in Example 10. The skilled artisan will recognize when an interfering functionality would make it desirable to do so.

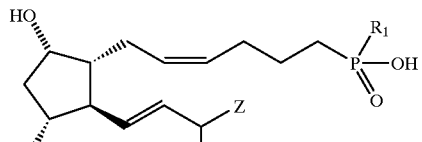

| Example | R$_1$ | Z |
|---|---|---|
| 11 | CH$_3$ | CH$_2$CH$_2$CH$_2$CH$_2$CH$_3$ |
| 12 | CH$_2$CH$_3$ | CH$_2$CH$_2$CH$_2$CH$_2$CH$_2$CH$_2$CH$_3$ |
| 13 | CH$_3$ | |

EXAMPLE 21

Preparation of 5-(3-hydroxy-4-phenoxybutyl)-4-(6-(methyl(hydroxyphosphoryl))hexyl)-1,3-diol, Sodium salt;

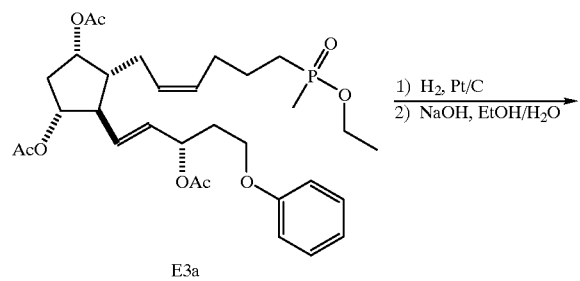

-continued

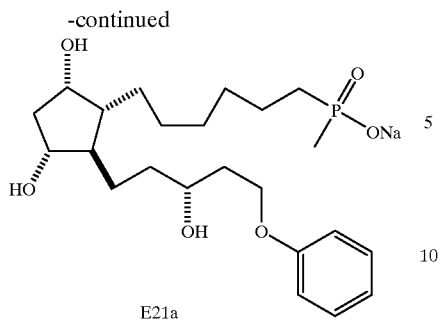

E21a

E3a is stirred at room temperature in ethanol in the presence of hydrogen gas and Pd/C (5% weight). The mixture is filtered twice to remove the Pd/C catalyst and diluted with a solution of NaOH in water. This is refluxed until the product is evident by thin-layer chromatography. The mixture is diluted with water and is washed with ethyl acetate (twice). The combined washes are extracted with water. The combined aqueous phases are acidified with 1 M aqueous hydrochloric acid and extracted with ethyl acetate (four times). The combined extracts are dried (brine, $Na_2SO_4$) and are evaporated. The residue is taken up in methanol and stirred with Amberlite CG-50 ($Na^+$ form) for 15 min. The resin is removed by filtration and the filtrate is concentrated to give the sodium salt 5-(3-hydroxy-4-phenoxybutyl)-4-(6-(methyl(hydroxyphosphoryl))hexyl) cyclopentane-1,3-diol, sodium salt (E21a).

EXAMPLES 22–31

Examples 22–31 are prepared using substantially the same procedure as that described Example 21, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

-continued

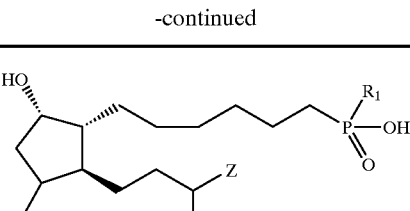

| Example | $R_1$ | Z |
|---|---|---|
| 23 | $CH_2CH_3$ | 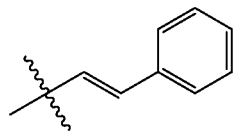 |
| 24 | $CH_3$ | 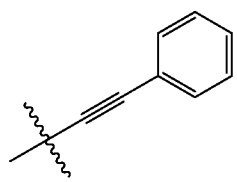 |
| 25 | $CH_3$ | 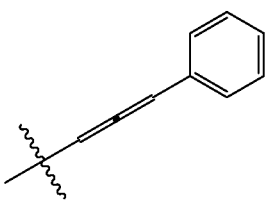 |
| 26 | $CH_3$ | 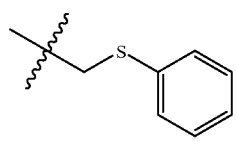 |
| 27 | $CH_3$ | 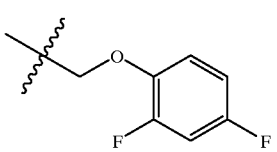 |
| 28 | $CH_2CH_3$ | 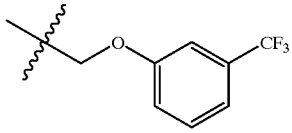 |
| 29 | $CH_3$ | 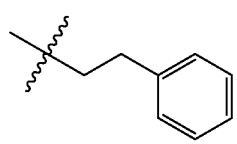 |

| Example | $R_1$ | Z |
|---|---|---|
| 22 | $CH_3$ | 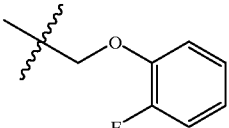 |

-continued

| Example | R₁ | Z |
|---|---|---|
| 30 | CH₃ | -CH₂-NH-Ph |
| 31 | H | -CH₂-NH-Ph |

EXAMPLE 32

Preparation of 5-(3-hydroxy-4-phenoxybutyl)-4-(6-(methyl(hydroxyphosphoryl))hexyl)-1-oxymyl-cyclopentan-3-ol, Sodium salt (E32a):

To a solution of Example 22 (1 equiv.) in THF is added ortho-2-bromo-benzyl bromide (0.9 equiv.) and sodium hydride. The mixture is refluxed until complete consumption of the benzyl bromide is achieved, as indicated by TLC. The reaction is quenched with NH₄OAc solution and the product extracted with EtOAc. The solvent is concentrated under vacuum, and the residue dissolved in ethanol. A solution of NaOH in water is added and the mixture is brought to reflux. The mixture is diluted with water and is washed with ethyl acetate twice. The combined washes are extracted with water. The combined aqueous phases are acidified with 1 M aqueous hydrochloric acid and extracted with ethyl acetate four times. The combined extracts are dried (brine, Na₂SO₄) and are evaporated. This material is then dissolved in toluene and heated to reflux with tri-n-butyl tin hydride. The reaction is monitored by TLC and when the starting material is gone the reaction is cooled to room temperature and the solvent removed. The organic extracts are combined and chromatographed and the crude product is stirred overnight with hydroxylamine and sodium acetate (1:9) in 1:1:3 p-dioxane: water: methanol. The residue is taken up in methanol and stirred with Amberlite CG-50 (Na⁺form) for 15 min. The resin is removed by filtration and the filtrate is concentrated to give 3-hydroxy-4-phenoxybutyl)-4-(6-(methyl(hydroxyphosphoryl))hexyl)-1-oxymyl-cyclopentan-3-ol, sodium salt (32b).

EXAMPLES 33–37

Examples 33–37 are prepared using substantially the same procedure as that described in Example 32, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

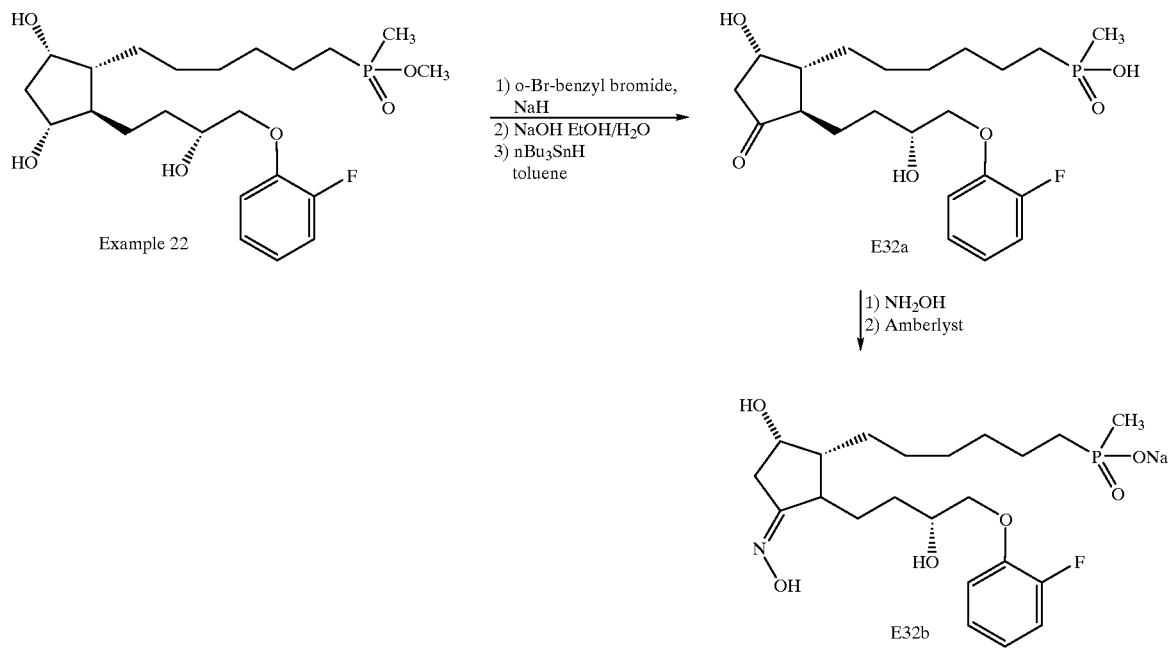

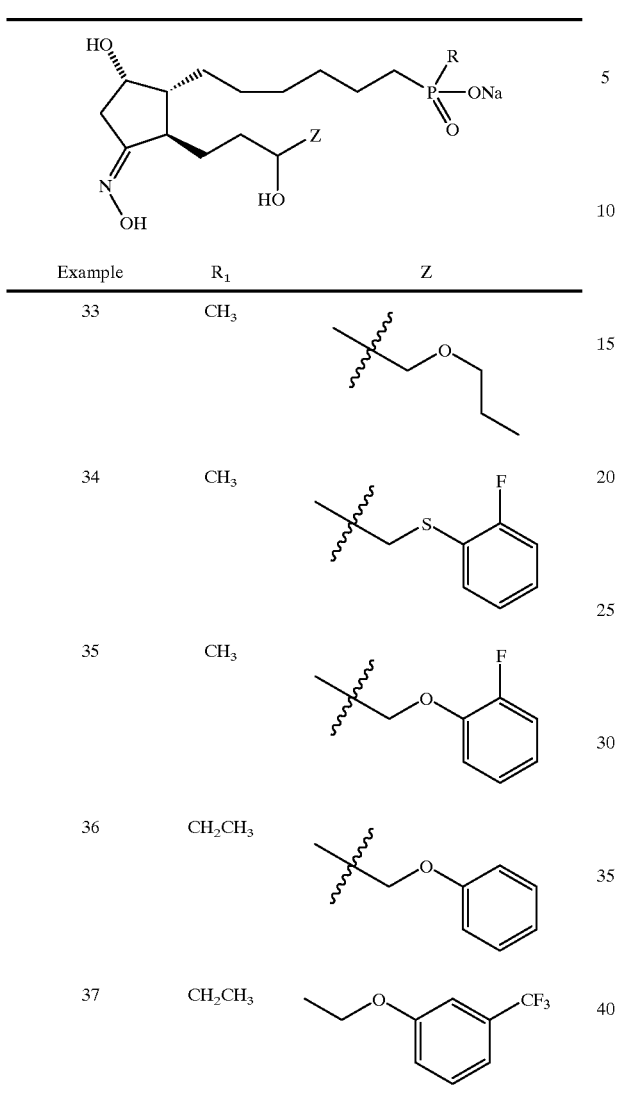

| Example | R₁ | Z |
|---|---|---|
| 33 | CH₃ | (propoxymethyl) |
| 34 | CH₃ | (2-fluorophenylthiomethyl) |
| 35 | CH₃ | (2-fluorophenoxymethyl) |
| 36 | CH₂CH₃ | (phenoxymethyl) |
| 37 | CH₂CH₃ | (3-(trifluoromethyl)phenoxyethyl) |

EXAMPLE 38

Preparation of 3-(3-hydroxy-4-(2-fluorophenoxy)butyl)-2-(6-(methyl(hydroxyphosphoryl))hexyl)-4-(hydroxyamino)-cyclopentan-1-ol, Sodium salt (E38a):

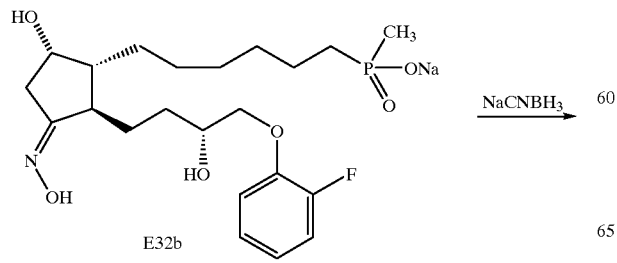

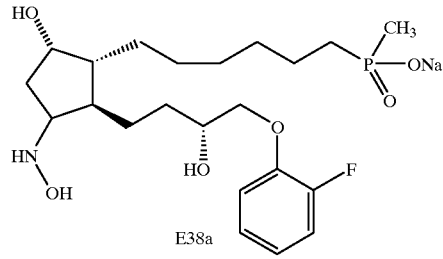

Compound E32b is treated with sodium cyanoborohydride in THF:acetic acid (1:1) and stirred for 2 hours. The mixture is quenched with 0.1 N HCl and washed with brine twice. The organic layer is dried over magnesium sulfate and concentrated. The resulting oil is chromatographed (30% ethyl acetate in hexanes). Appropriate fractions are combined and concentrated yielding the hydroxylamine. Salt formation is accomplished by methods described above, yielding 3-(3-hydroxy-4-(2-fluorophenoxy)butyl)-2-(6-(methyl(hydroxyphosphoryl))hexyl)-4-(hydroxyamino)-cyclopentan-1-ol, Sodium salt (E38a).

EXAMPLES 39–44

Examples 39–44 are prepared using substantially the same procedure as that described in Example 38, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

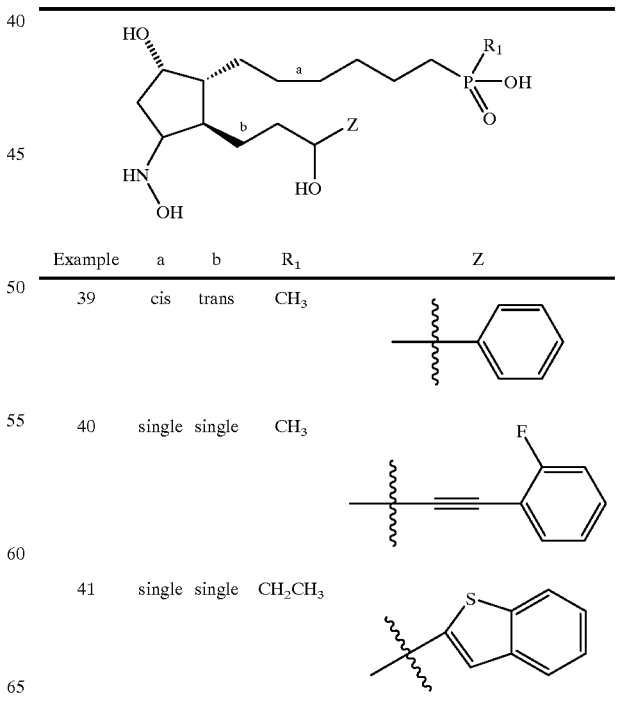

| Example | a | b | R₁ | Z |
|---|---|---|---|---|
| 39 | cis | trans | CH₃ | (phenyl) |
| 40 | single | single | CH₃ | (2-fluorophenylethynyl) |
| 41 | single | single | CH₂CH₃ | (benzothiophen-2-yl) |

-continued

| Example | a | b | R₁ | Z |
|---|---|---|---|---|
| 42 | single | single | $CH_2CH_3$ | -CH₂-NH-C₆H₅ |
| 43 | cis | trans | $CH_2CH_3$ | -CH₂-S-(thiophene-S-2,3-dichloro) |
| 44 | single | single | $CH(CH_3)_2$ | -CH₂-S-(2-fluorophenyl) |

Compositions

Compositions of the subject invention comprise a safe and effective amount of the subject compounds, and a pharmaceutically—acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of the treatment, the nature of concurrent therapy, the particular pharmaceutically—acceptable carrier utilized, and like factors within the knowledge and expertise of the attending physician.

In addition to the compound, the compositions of the subject invention contain a pharmaceutically—acceptable carrier. The term "pharmaceutically—acceptable carrier", as used herein, means one or more compatible solid or liquid filler diluents or encapsulating substances which are suitable for administration to a subject. The term "compatible", as used herein, means that the components of the composition are capable of being commingled with the compound, and with each other, in a manner such that there is no interaction which would substantially reduce the pharmaceutical efficacy of the composition under ordinary use situations. Pharmaceutically—acceptable carriers must, of course, be of sufficiently high purity and sufficiently low toxicity to render them suitable for administration to the subject being treated.

Some examples of substances which can serve as pharrnaceutically—acceptable carriers or components thereof are sugars, such as lactose, glucose and sucrose; starches, such as cornstarch and potato starch; cellulose and its derivatives, such as sodium carboxymethyl cellulose, ethyl cellulose, cellulose acetate; powdered tragacanth; malt; gelatin; talc; solid lubricants, such as stearic acid, magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the Tweens®; wetting agents such as sodium lauryl sulfate; coloring agents; flavoring agents; excipients; tableting agents; stabilizers; antioxidants; preservatives; pyrogen-free water; isotonic saline; and phosphate buffer solutions.

The choice of a pharmaceutically—acceptable carrier to be used in conjunction with a compound is basically determined by the way the compound is to be administered. The compounds of the present invention may be administered systemically. Routes of administration include transdermal; oral; parenterally, including subcutaneous or intravenous injection; topical; and/or intranasal.

The appropriate amount of the compound to be used may be determined by routine experimentation with animal models. Such models include, but are not limited to the intact and ovariectomized rat models, the ferret, canine, and non human primate models as well as disuse models.

Preferred unit dosage forms for injection include sterile solutions of water, physiological saline, or mixtures thereof. The pH of said solutions should be adjusted to about 7.4. Suitable carriers for injection or surgical implants include hydrogels, controlled—or sustained release devises, polylactic acid, and collagen matrices.

Suitable pharmaceutically—acceptable carriers for topical application include those suited for use in lotions, creams, gels and the like. If the compound is to be administered perorally, the preferred unit dosage form is tablets, capsules and the like. The pharmaceutically—acceptable carriers suitable for the preparation of unit dosage forms for oral administration are well-known in the art. Their selection will depend on secondary considerations like taste, cost, and shelf stability, which are not critical for the purposes of the subject invention, and can be made without difficulty by those skilled in the art.

Methods of Use

The compounds of the present invention are useful in treating many medical disorders, including for example, bone disorders and ocular disorders.

It is believed that the compounds of the present invention are useful in increasing bone volume and trabecular number through formation of new trabeculae, increasing bone mass while maintaining a normalized bone turnover rate, and formation of bone at the endosteal surface without removing bone from the existing cortex. Thus, it is further believed that these compounds are useful in the treatment and prevention of bone disorders.

The preferred routes of administration for treating bone disorders are oral, transdermal, and intranasal. Other preferred routes of administration include rectal, and sublingual.

The dosage range of the compound for systemic administration is from about 0.01 to about 1000 µ/kg body weight, preferably from about 0.1 to about 100 µg/kg per body weight, most preferably from about 1 to about 50 µg/kg body weight per day. The transdermal dosages will be designed to attain similar serum or plasma levels, based upon techniques known to those skilled in the art of pharmacokinetics and transdermal formulations. Plasma levels for systemic administration are expected to be in the range of 0.01 to 100 nanograms/ml, more preferably from 0.05 to 50 ng/ml, and most preferably from 0.1 to 10 ng/ml. While these dosages are based upon a daily administration rate, weekly or monthly accumulated dosages may also be used to calculate the clinical requirements.

Dosages may be varied based on the patient being treated, the condition being treated, the severity of the condition being treated, the route of administration, etc. to achieve the desired effect.

The compounds of the present invention are also useful in decreasing intraocular pressure. Thus, these compounds are useful in the treatment of glaucoma. The preferred route of administration for treating glaucoma is topically.

Composition and Method Examples

The following non-limiting examples illustrate the compositions and methods of the present invention. The following composition and method examples do not limit the invention, but provide guidance to the skilled artisan to prepare and use the compounds, compositions and methods of the invention. In each case other compounds within the invention may be substituted for the example compound shown below with similar results. The skilled practitioner will appreciate that the examples provide guidance and may be varied based on the condition being treated and the patient.

Example A

Pharmaceutical compositions in the form of tablets are prepared by conventional methods, such as mixing and direct compression, formulated as follows:

| Ingredient | Quantity (mg per tablet) |
| --- | --- |
| Compound of Example I | 5 |
| Microcrystalline Cellulose | 100 |
| Sodium Starch Glycollate | 30 |
| Magnesium Stearate | 3 |

When administered orally once daily, the above composition substantially increases bone volume in a patient suffering from osteoporosis.

Example B

Pharmaceutical compositions in liquid form are prepared by conventional methods, formulated as follows:

| Ingredient | Quantity |
| --- | --- |
| Compound of Example 1 | 5 mg |
| Phosphate buffered physiological saline | 10 mL |
| Methyl Paraben | 0.05 mL |

When 1.0 mL of the above composition is administered subcutaneously once daily, the above composition substantially increases bone volume in a patient suffering from osteoporosis.

Example C

Topical pharmaceutical compositions for lowering intraocular pressure are prepared by conventional methods and formulated as follows:

| Ingredient | Amount (wt %) |
| --- | --- |
| Compound of Example 14 | 0.004 |
| Dextran 70 | 0.1 |
| Hydroxypropyl methylcellulose | 0.3 |
| Sodium Chloride | 0.77 |
| Potassium chloride | 0.12 |
| Disodium FDTA (Edetate disodium) | 0.05 |
| Benzalkonium chloride | 0.01 |
| HCl and/or NaOH | pH 7.2–7.5 |
| Purified water | q.s. to 100% |

When 1 drop of the above composition is administered to each affected eye twice daily, the above composition substantially decreases intraocular pressure in a patient suffering from glaucoma.

While particular embodiments of the subject invention have been described, it would be obvious to those skilled in the art that various changes and modifications to the compositions disclosed herein can be made without departing from the spirit and scope of the invention. It is intended to cover, in the appended claims, all such modifications that are within the scope of this invention.

What is claimed is:

1. A compound having the following structure:

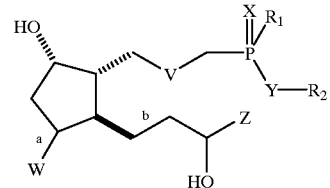

wherein $R_1$ is H or lower alkyl;

$R_2$ is H, alkyl, heteroalkyl, carbocyclic aliphatic ring, heterocyclic aliphatic ring, aromatic ring, or heteroaromatic ring;

X is O or S;

Y is O, S or NH;

V is $C_4$ alkyl or $M_4$ heteroalkyl;

a is single bond, cis double bond, or trans double bond;

b is single bond, trans double bond, or triple bond;

when a is single bond, W is OH or $N(R_3)(OR_4)$; wherein $R_3$ is selected from H, lower alkyl, or lower heteroalkyl; wherein said lower alkyl is unsubstituted or substituted with from 1 to about 3 substituents selected from the group consisting of: hydroxyl, halo, thiol, and nitrile; and wherein said lower heteroalkyl is unsubstituted or substituted with from 1 to about 3 substituents selected from the group consisting of: hydroxyl, halo, thiol, and nitrile; and $R_4$ is H, lower alkyl, or lower heteroalkyl;

when a is cis double bond or trans double bond, W is $N(OR_4)$; wherein $R_4$, is as defined above;

Z is $C_1$ alkyl, $M_1$ heteroalkyl, $C_m$ alkyl-G', $M_n$ heteroalkyl-G', $C_p$ alkyl-G", or $M_q$ heteroalkyl-G"; wherein l is an integer from about 3 to about 7; m is an integer from 0 to about 5; n is an integer from about 2 to about 5; p is an integer from 0 to about 3; q is 2 or 3; G' is monocyclic carbocyclic aliphatic ring, monocyclic heterocyclic aliphatic ring, monocyclic aromatic ring or monocyclic heteroaromatic ring; G" is bicyclic carbocyclic aliphatic ring, bicyclic heterocyclic aliphatic ring, bicyclic aromatic ring or bicyclic heteroaromatic ring; and any pharmaceutically—acceptable salt, or biohydrolyzable amide, ester, or imide thereof.

2. A compound according to claim 1 wherein $R_1$ is methyl or ethyl and $R_2$ is H or lower alkyl.

3. A compound according to claim 2 wherein X is O, Y is O or NH, and V is $C_4$ alkyl.

4. A compound according to claim 3 wherein Z is $C_m$ alkyl-G' or $M_n$ heteroalkyl-G' and said G' is monocyclic aromatic ring or monocyclic heteroaromatic ring.

5. A compound according to claim 3 wherein Z is $C_p$ alkyl-G" or $M_q$ heteroalkyl-G" and said G'" is bicyclic aromatic ring or bicyclic heteroaromatic ring.

6. A method of treating a human or other animal subject having a bone disorder, said method comprising administering to said subject a compound according to the structure:

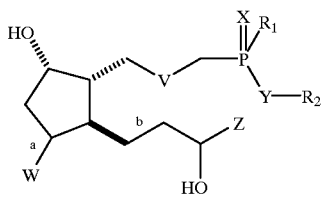

wherein $R_1$ is H or lower alkyl;

$R_2$ is H, alkyl, heteroalkyl, carbocyclic aliphatic ring, heterocyclic aliphatic ring, aromatic ring, or heteroaromatic ring;

X is O or S;

Y is O, S or NH;

V is $C_4$ alkyl or $M_4$ heteroalkyl;

a is single bond, cis double bond, or trans double bond;

b is single bond, trans double bond, or triple bond;

when a is single bond, W is OH or $N(R_3)(OR_4)$; wherein $R_3$ is selected from H, lower alkyl, or lower heteroalkyl; wherein said lower alkyl is unsubstituted or substituted with from 1 to about 3 substituents selected from the group consisting of: hydroxyl, halo, thiol, and nitrile; and wherein said lower heteroalkyl is unsubstituted or substituted with from 1 to about 3 substituents selected from the group consisting of: hydroxyl, halo, thiol, and nitrile; and $R_4$ is H, lower alkyl, or lower heteroalkyl;

when a is cis double bond or trans double bond, W is $N(OR_4)$; wherein $R_4$, is as defined above;

Z is $C_1$ alkyl, $M_1$ heteroalkyl, $C_m$ alkyl-G', $M_n$ heteroalkyl-G', $C_p$ alkyl-G", or $M_q$ heteroalkyl-G"'; wherein l is an integer from about 3 to about 7; m is an integer from 0 to about 5; n is an integer from about 2 to about 5; p is an integer from 0 to about 3; q is 2 or 3; G' is monocyclic carbocyclic aliphatic ring, monocyclic heterocyclic aliphatic ring, monocyclic aromatic ring or monocyclic heteroaromatic ring; G" is bicyclic carbocyclic aliphatic ring, bicyclic heterocyclic aliphatic ring, bicyclic aromatic ring or bicyclic heteroaromatic ring; and any pharmaceutically—acceptable salt, or biohydrolyzable amide, ester, or imide thereof.

7. The method of claim 6 wherein said bone disorder is osteoporosis.

8. The method of claim 7 wherein said bone disorder is post-menopausal osteoporosis.

9. The method of claim 7. wherein said bone disorder is cortico-steroid induced osteoporosis.

10. The method of claim 6 wherein said bone disorder is osteopenia.

11. The method of claim 6 wherein said bone disorder is a bone fracture.

12. The method of claim 6 wherein said compound is administered orally.

13. A method of treating glaucoma, said method comprising administering to a human or other animal a safe and effective amount of a compound according to the structure:

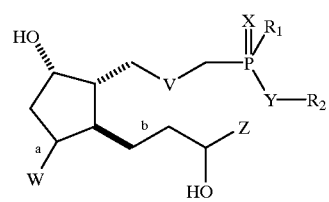

wherein $R_1$ is H or lower alkyl;

$R_2$ is H, alkyl, heteroalkyl, carbocyclic aliphatic ring, heterocyclic aliphatic ring, aromatic ring, or heteroaromatic ring;

X is O or S;

Y is O, S or NH;

V is $C_4$ alkyl or $M_4$ heteroalkyl;

a is single bond, cis double bond, or trans double bond;

b is single bond, trans double bond, or triple bond;

when a is single bond, W is OH or $N(R_3)(OR_4)$; wherein $R_3$ is selected from H, lower alkyl, or lower heteroalkyl; wherein said lower alkyl is unsubstituted or substituted with from 1 to about 3 substituents selected from the group consisting of: hydroxyl, halo, thiol, and nitrile; and wherein said lower heteroalkyl is unsubstituted or substituted with from 1 to about 3 substituents selected from the group consisting of: hydroxyl, halo, thiol, and nitrile; and $R_4$ is H, lower alkyl, or lower heteroalkyl;

when a is cis double bond or trans double bond, W is $N(OR_4)$; wherein $R_4$, is as defined above;

Z is $C_1$ alkyl, $M_1$ heteroalkyl, $C_m$ alkyl-G', $M_n$ heteroalkyl-G', $C_p$ alkyl-G", or $M_q$ heteroalkyl-G"; wherein l is an integer from about 3 to about 7; m is an integer from 0 to about 5; n is an integer from about 2 to about 5; p is an integer from 0 to about 3; q is 2 or 3; G' is monocyclic carbocyclic aliphatic ring, monocyclic heterocyclic aliphatic ring, monocyclic aromatic ring or monocyclic heteroaromatic ring; G" is bicyclic carbocyclic aliphatic ring, bicyclic heterocyclic aliphatic ring, bicyclic aromatic ring or bicyclic heteroaromatic ring; and any pharmaceutically—acceptable salt, or biohydrolyzable amide, ester, or imide thereof.

14. The method of claim 13 wherein said compound is administered topically.

* * * * *

UNITED STATES PATENT AND TRADEMARK OFFICE
CERTIFICATE OF CORRECTION

PATENT NO. : 6,372,730 B1 Page 1 of 1
DATED : April 16, 2002
INVENTOR(S) : Mitchell Anthony deLong et al.

It is certified that error appears in the above-identified patent and that said Letters Patent is hereby corrected as shown below:

Column 3,
Line 56, delete "staurated" and insert -- saturated --.

Column 6,
Line 33, delete "staurated" and insert -- saturated --.

Column 15,
Line 11, delete "hydroxy4" and insert -- hydroxy-4 --.
Line 13, delete "E1Oe" and insert -- E10e --.
Line 13, delete "E1Od" and insert -- E10d --.

Signed and Sealed this

Thirtieth Day of December, 2003

JAMES E. ROGAN
*Director of the United States Patent and Trademark Office*